(12) United States Patent
Old et al.

(10) Patent No.: US 7,960,381 B2
(45) Date of Patent: *Jun. 14, 2011

(54) SUBSTITUTED GAMMA LACTAMS AS THERAPEUTIC AGENTS

(75) Inventors: David W. Old, Irvine, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/524,803

(22) PCT Filed: Jan. 29, 2008

(86) PCT No.: PCT/US2008/052318
§ 371 (c)(1),
(2), (4) Date: Jul. 28, 2009

(87) PCT Pub. No.: WO2008/094912
PCT Pub. Date: Aug. 7, 2008

(65) Prior Publication Data
US 2010/0093729 A1    Apr. 15, 2010

Related U.S. Application Data

(60) Provisional application No. 60/887,415, filed on Jan. 31, 2007.

(51) Int. Cl.
| | |
|---|---|
| *A61K 31/422* | (2006.01) |
| *A61K 31/421* | (2006.01) |
| *A61K 31/427* | (2006.01) |
| *A61K 31/4025* | (2006.01) |
| *A61K 31/4015* | (2006.01) |
| *C07D 413/12* | (2006.01) |
| *C07D 413/06* | (2006.01) |
| *C07D 417/06* | (2006.01) |
| *C07D 417/12* | (2006.01) |
| *C07D 405/12* | (2006.01) |
| *C07D 405/06* | (2006.01) |

(52) U.S. Cl. ............... 514/237.2; 514/365; 514/369; 514/374; 514/376; 514/422; 544/141; 548/236; 548/527; 548/551; 548/517; 548/186; 548/204

(58) Field of Classification Search .................... None
See application file for complete search history.

(56) References Cited

U.S. PATENT DOCUMENTS
6,710,072 B2 * 3/2004 Burk et al. ............... 514/438
7,091,231 B2    8/2006 Donde et al.

FOREIGN PATENT DOCUMENTS
| EP | 1 481 976 | 12/2004 |
|---|---|---|
| WO | WO 03/103604 | 12/2003 |
| WO | WO 2007-109578 | 9/2007 |

OTHER PUBLICATIONS

U.S. Appl. No. 12/524,803, filed Jul. 2009, Old, David.*
U.S. Appl. No. 10/599,046, filed Sep. 18, 2006, David Old, et al.
U.S. Appl. No. 60/777,506, filed Feb. 28, 2006, David Old, et al.
U.S. Appl. No. 60/894,267, filed Mar. 12, 2007, Michael E. Garst, et al.

* cited by examiner

*Primary Examiner* — Yong Chu
*Assistant Examiner* — Michael Barker
(74) *Attorney, Agent, or Firm* — Kevin J. Forrestal; John E. Wurst; Doina G. Ene

(57) ABSTRACT

A compound comprising or a pharmaceutically acceptable salt, prodrug, or a metabolite thereof is disclosed herein. Y, A, and B are as described herein. Methods, compositions, and medicaments related to these compounds are also disclosed.

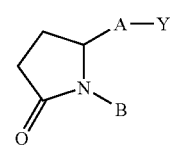

(I)

16 Claims, No Drawings

SUBSTITUTED GAMMA LACTAMS AS THERAPEUTIC AGENTS

CROSS REFERENCE TO RELATED APPLICATIONS

This is a national stage application under 35 U.S.C. 371 of PCT patent application PCT/US2008/052318, filed on Jan. 29, 2008, which claims the benefit of U.S. Provisional Patent Application 60/887,415, filed Jan. 31, 2007, each of which is hereby incorporated by reference in its entirety.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

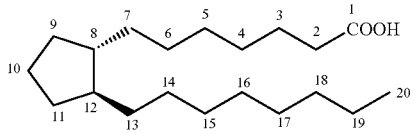

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

A compound is disclosed herein comprising

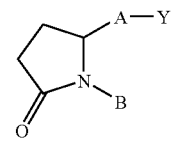

or a pharmaceutically acceptable salt, thereof;
wherein Y is
—CO₂(CH₂)₂OH or

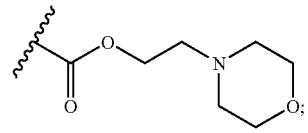

A is —(CH₂)₆—, cis —CH₂CH═CH—(CH₂)₃—, or —CH₂C═C—(CH₂)₃—, wherein 1 or 2 carbon atoms may be replaced by S or O; or A is —(CH₂)$_m$—Ar—(CH₂)$_o$— wherein Ar is interarylene or heterointerarylene, the sum of m and o is 1, 2, 3, or 4, and wherein 1 —CH₂— may be replaced by S or O, and 1 —CH₂—CH₂ may be replaced by —CH═CH— or C≡C; and
B is aryl or heteroaryl.
Y is —OC₂(CH₂)₂OH or

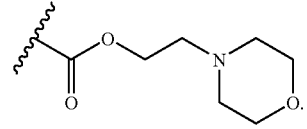

Thus, the following compounds are contemplated.

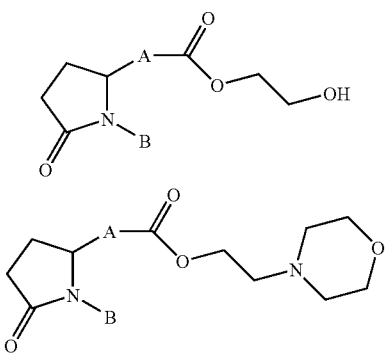

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced by S or O; or A is —(CH$_2$)$_m$—Ar—(CH$_2$)$_o$— wherein Ar is interarylene or heterointerarylene, the sum of m and o is 1, 2, 3, or 4, and wherein 1 —CH$_2$— may be replaced by S or O, and 1 —CH$_2$—CH$_2$ may be replaced by —CH=CH— or C≡C—.

Thus, while not intending to be limiting, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is replaced with S or O. For example, while not intending to limit the scope of the invention in any way, A may be a moiety where S replaces one or two carbon atoms such as one of the following or the like.

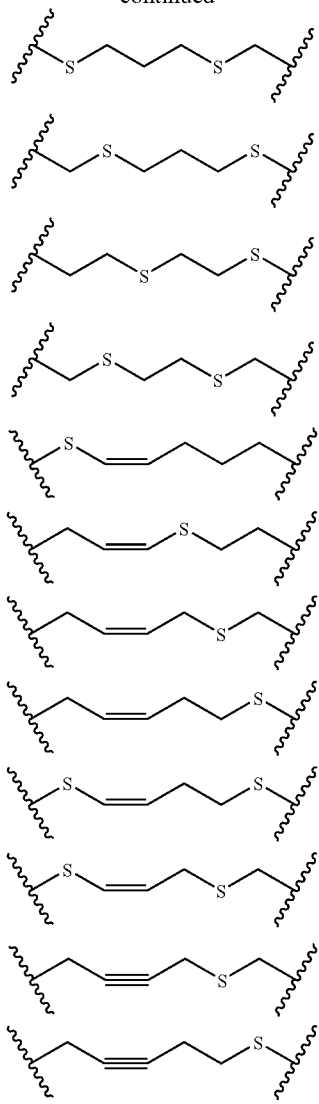

Alternatively, while not intending to limit the scope of the invention in any way, A may be a moiety where O replaces one or two carbon atoms such as one of the following or the like.

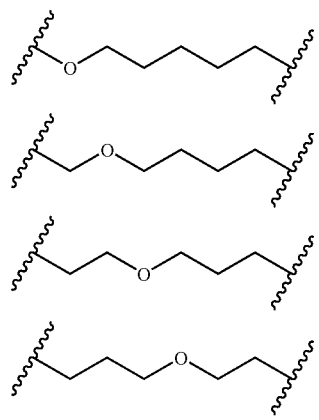

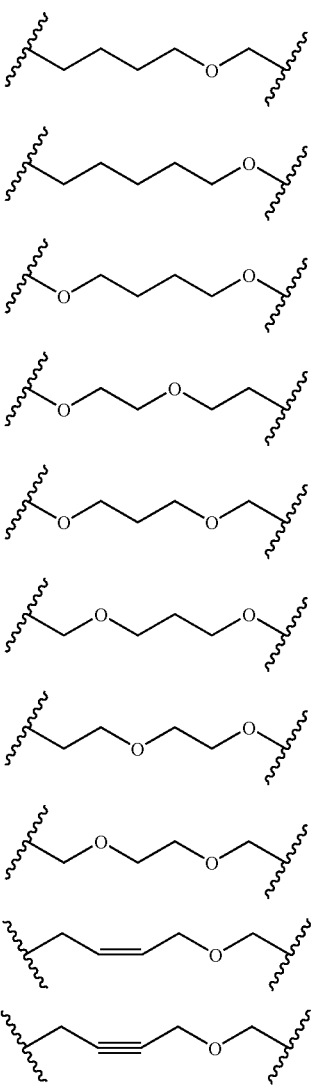

Alternatively, while not intending to limit the scope of the invention in any way, A may have an O replacing one carbon atom and an S replacing another carbon atom, such as one of the following or the like.

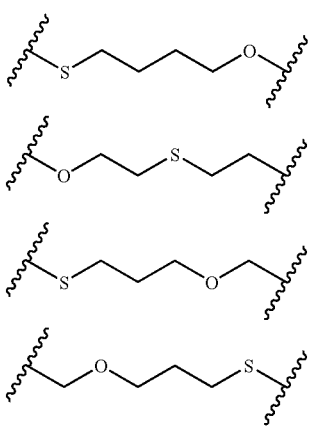

Alternatively, while not intending to limit the scope of the invention in any way, in certain embodiments A is —$(CH_2)_m$—Ar—$(CH_2)_o$— wherein Ar is interarylene or heterointerarylene, the sum of m and o is 1, 2, 3, or 4, and wherein 1 —$CH_2$— may be replaced by S or O, and 1 —$CH_2$—$CH_2$— may be replaced by —CH=CH— or —C≡C—. In other words, while not intending to limit the scope of the invention in any way,
in one embodiment A comprises:
 1) a) 1, 2, 3, or 4 $CH_2$ moieties, or
    b) 0, 1 or 2 $CH_2$ moieties and —CH=CH— or —CH≡CH—; and
 2) Ar;
e.g. —$CH_2$—Ar—, —$(CH_2)_2$—Ar—, —CH=CH—Ar—, C≡C—Ar—, —$CH_2$—Ar—$CH_2$—, —$CH_2$Ar—$(CH_2)_2$—, —$CH_2$Ar—CH=CH—, —$CH_2$Ar—C≡C—, —$(CH_2)_2$—Ar—$(CH_2)_2$—, and the like;
in another embodiment A comprises:
 1) a) O; and 0, 1, 2, or 3 $CH_2$ moieties; or
    b) O; and 0 or 1 $CH_2$ moieties and —CH=CH— or —C≡C—; and
 2) Ar;
e.g., —O—Ar—, Ar—$CH_2$—O—, —O—Ar—$(CH_2)_2$—, —OAr—CH=CH—, —O—Ar—C≡C—, —O—$CH_2$—Ar—, —O—$CH_2$—Ar—$(CH_2)_2$, —O—$CH_2$Ar—CH=CH—, —O—$CH_2$Ar—C≡C—, and the like; or
in another embodiment A comprises:
 1) a) S; and 0, 1, 2, or 3 $CH_2$ moieties; or
    b) S; and 0 or 1 $CH_2$ moieties and —CH=CH— or —C≡C—; and
 2) Ar;
e.g., —S—Ar—, Ar—$CH_2$—S—, —S—Ar—$(CH_2)_2$—, —S—Ar—CH=CH—, —S—Ar—C≡C—; —S—$CH_2$—Ar—, —S—$CH_2$—Ar—$(CH_2)_2$, —S—$CH_2$Ar—CH=CH—, —S—$CH_2$Ar—C≡C—, and the like.

In another embodiment, the sum of m and o is 2, 3, or 4 wherein one $CH_2$ may be replaced with S or O and 1 —$CH_2$—$CH_2$— may be replaced by —CH=CH— or —C≡C—.

In another embodiment, the sum of m and o is 3 wherein one $CH_2$ may be replaced with S or O and 1 —$CH_2$—$CH_2$— may be replaced by —CH=CH— or —C≡C—.

In another embodiment, the sum of m and o is 2 wherein one $CH_2$ may be replaced with S or O or 1 —$CH_2$—$CH_2$— may be replaced by —CH=CH— or —C≡C—.

In another embodiment, the sum of m and o is 4 wherein one $CH_2$ may be replaced with S or O and 1 —$CH_2$—$CH_2$— may be replaced by —CH=CH— or —C≡C—.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2$$^-$K$^-$ salt. Any cation of the salt is not counted in the "4 or less heavy atoms." Thus, the substituent may be hydrocarbyl, i.e. a moiety consisting of only carbon and hydrogen, including linear, branched or cyclic hydrocarbyl, and combinations thereof; having up to 4 carbon atoms, including alkyl up to C$_4$, alkenyl, alkynyl, and the like;

hydrocarbyloxy, i.e. —O-hydrocarbyl, up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$-Ph-(CH$_2$)$_o$— wherein the sum of m and o is 1, 2, or 3, and wherein one CH$_2$ may be replaced with S or O.

In another embodiment A is —CH$_2$—Ar—OCH$_2$—. In another embodiment A is —CH$_2$-Ph-OCH$_2$—. In another embodiment, Ph is attached at the 1 and 3 positions, otherwise known as m-interphenylene, such as when A has the structure shown below.

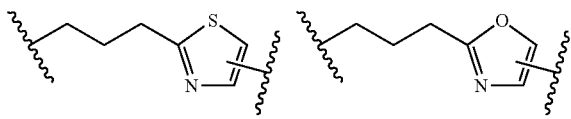

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In one embodiment, Ar is thienyl.

In other embodiments, A has one of the following structures.

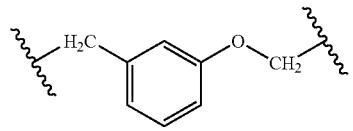

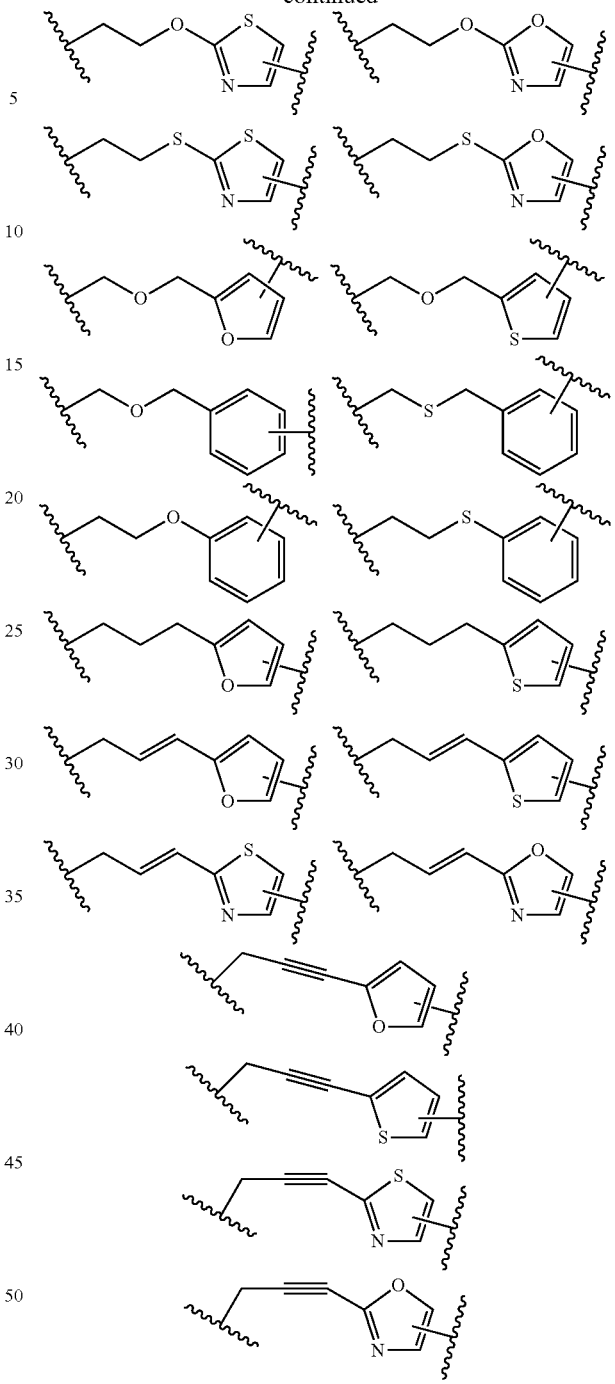

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH=CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH=CH—CH$_2$OCH$_2$—.

In another embodiment A is —CH₂CH═CH—OCH₂—.
In another embodiment A is —(CH₂)₂S(CH₂)₃—.
In another embodiment A is —CH₂-Ph-OCH₂—, wherein Ph is interphenylene.
In another embodiment A is —CH₂-mPh-OCH₂—, wherein mPh is m-interphenylene.
In another embodiment A is —CH₂—O—(CH2)₄—.
In another embodiment A is —CH₂—O—CH₂—Ar—, wherein Ar is 2,5-interthienylene.
In another embodiment A is —CH₂—O—CH₂—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-(methoxymethyl)phenyl.
In another embodiment A is 3-(3-propylphenyl).
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.
B is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:

hydrocarbyl, i.e. a moiety consisting of only carbon and hydrogen such as alkyl, alkenyl, alkynyl, and the like, including linear, branched or cyclic hydrocarbyl, and combinations thereof;
hydrocarbyloxy, meaning O-hydrocarbyl such as OCH₃, OCH₂CH₃, O-cyclohexyl, etc, up to 11 carbon atoms;
other ether substituents such as CH₂OCH₃, (CH₂)₂OCH(CH₃)₂, and the like;
thioether substituents including S-hydrocarbyl and other thioether substituents;
hydroxyhydrocarbyl, meaning hydrocarbyl-OH such as CH₂OH, C(CH₃)₂OH, etc, up to 11 carbon atoms;
nitrogen substituents such as NO₂, CN, and the like, including amino, such as NH₂, NH(CH₂CH₃OH), NHCH₃, and the like up to 11 carbon atoms;
carbonyl substituents, such as CO₂H, ester, amide, and the like;
halogen, such as chloro, fluoro, bromo, and the like
fluorocarbyl, such as CF₃, CF₂CF₃, etc.;
phosphorous substituents, such as PO₃²⁻, and the like;
sulfur substituents, including S-hydrocarbyl, SH, SO₃H, SO₂-hydrocarbyl, SO₃-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Substituted aryl or heteroaryl may have one or more substituents, up to as many as the ring or ring system will bear, and the substituents may be the same or different. Thus, for example, an aryl ring or a heteroaryl ring may be substituted with chloro and methyl; methyl, OH, and F; CN, NO₂, and ethyl; and the like including any conceivable substituent or combination of substituent possible in light of this disclosure.

Thus, compounds wherein B is any of the above classes or species of aryl or heteroaryl are contemplated herein.

Further, while not intending to limit the scope of the invention in any way, in one embodiment B is phenyl. In another embodiment B is chlorophenyl, meaning phenyl with one or more chloro substituents. In another embodiment D is 3,5-dichlorophenyl. In another embodiment B is unsubstituted phenyl. In another embodiment B is alkylphenyl. In another embodiment B is t-butylphenyl.

In another embodiment B is not unsubstituted phenyl. In another embodiment B is not chlorophenyl. In another embodiment B is not fluorophenyl. In another embodiment B is not dimethylaminophenyl. In another embodiment B is not unsubstituted phenyl, chlorophenyl, fluorophenyl, or dimethylaminophenyl.

In another embodiment B is hydroxyalkylphenyl, meaning phenyl with a hydroxyalkyl substitutuent such as Ph-CH(OH)C(CH₃)₃.

B can also be any of the groups shown below, where the remainder of the molecule attaches to the phenyl ring. The names of these moieties are shown to the right of the structure.

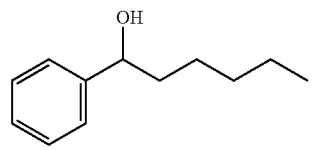
(1-hydroxyhexyl)phenyl

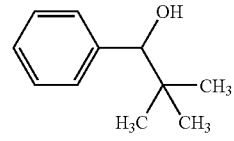
(1-hydroxy-2,2-dimethylpropyl)phenyl

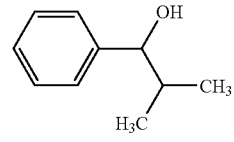
(1-hydroxy-2-methylpropyl)phenyl

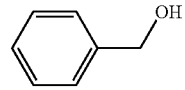
(hydroxymethyl)phenyl

-continued

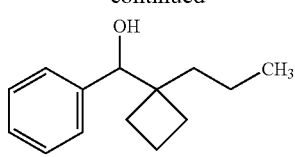
[(1-propylcyclobutyl)hydroxymethyl]phenyl

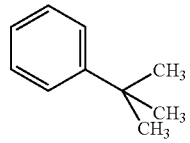
t-butylphenyl

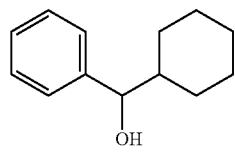
(cyclohexylhydroxymethyl)phenyl

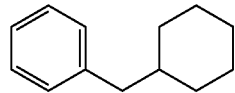
(cyclohexylmethyl)phenyl

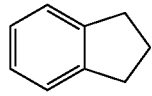
indanyl

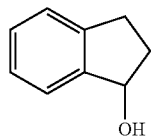
indanolyl

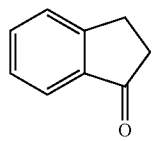
indanonyl

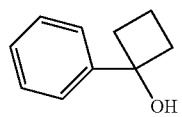
(1-hydroxycyclobutyl)phenyl

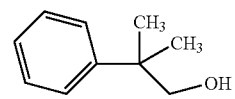
(2-methyl-3-hydroxypropyl)phenyl

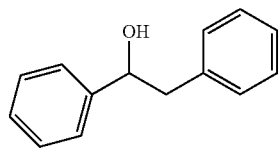
(1-hydroxy-2-phenylethyl)phenyl

One compound comprises

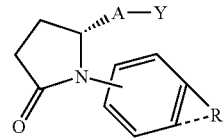

or a pharmaceutically acceptable salt, prodrug, or a metabolite thereof;
wherein a dashed line indicates the presence or absence of a bond
R is hydrocarbyl or hydroxyhydrocarbyl having from 1 to 12 carbon atoms.

Another embodiment comprises

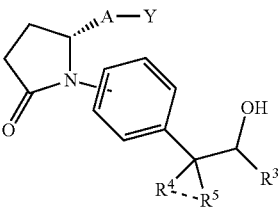

or a pharmaceutically acceptable salt, prodrug, or a metabolite thereof;
wherein a dashed line indicates the presence or absence of a bond;
$R^3$, $R^4$, and $R^5$ are independently H or $C_{1-6}$ alkyl.

As the dashed line indicates the presence or absence of a bond, $R^4$ and $R^5$ may be two separate moieties. For example, while not intending to be limiting, in one embodiment $R^4$ and $R^5$ is methyl, and no bond is present where indicated by the dashed line.

For example, a compound according to the formula below

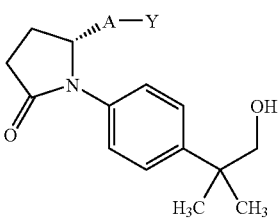

or a pharmaceutically acceptable salt, prodrug, or a metabolite thereof is contemplated. Alternatively, while not intending to limit the scope of the invention in any way, $R^4$ and $R^5$ may form a ring. In other words, a compound such as the one shown below is possible, wherein x is from 1 to 6.

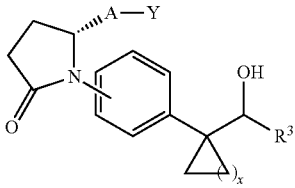

A pharmaceutically acceptable salt, prodrug, or a metabolite thereof is also contemplated.

Another embodiment comprises

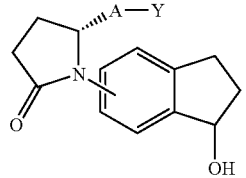

A pharmaceutically acceptable salt, prodrug, or a metabolite thereof is also contemplated.

Other useful compounds comprise

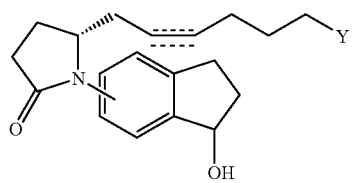

A pharmaceutically acceptable salt, prodrug, or a metabolite thereof is also contemplated.

Other useful examples of compounds comprise

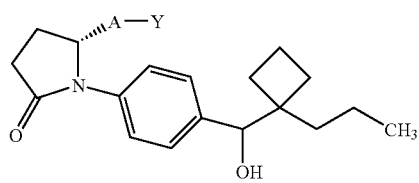

or a pharmaceutically acceptable salt, prodrug, or a metabolite thereof.

Other compounds comprise

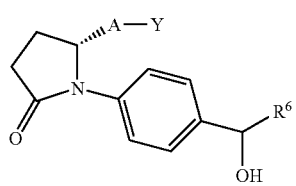

or a pharmaceutically acceptable salt, prodrug, or a metabolite thereof, wherein $R^6$ is cycloalkyl comprising from 3 to 10 carbon atoms.

Other compounds comprise

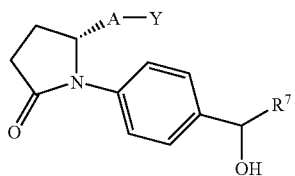

or a pharmaceutically acceptable salt, prodrug, or a metabolite thereof, wherein $R^7$ is linear alkyl comprising from 3 to 7 carbon atoms.

Other compounds comprise

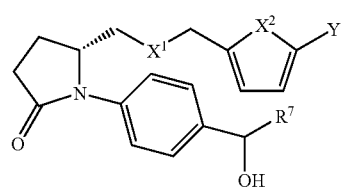

or a pharmaceutically acceptable salt, prodrug, or a metabolite thereof, wherein $X^1$ and $X^2$ are independently CH, O, or S; and $R^7$ is linear alkyl comprising from 3 to 7 carbon atoms.

Other compounds comprise

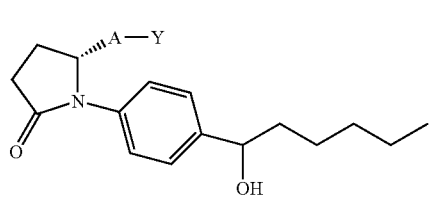

or a pharmaceutically acceptable salt, prodrug, or a metabolite thereof.

Other compounds comprise

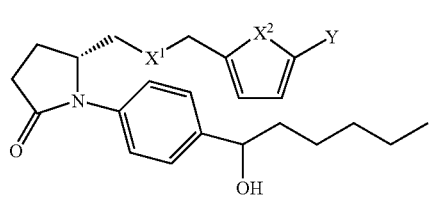

or a pharmaceutically acceptable salt, prodrug, or a metabolite thereof, wherein $X^1$ and $X^2$ are independently CH, O, or S.

Other compounds comprise

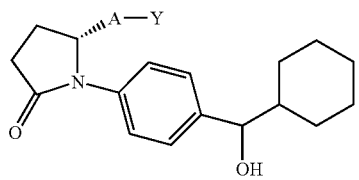

or a pharmaceutically acceptable salt, prodrug, or a metabolite thereof.

Other compounds comprise

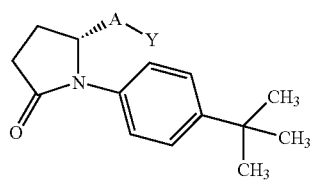

or a pharmaceutically acceptable salt, prodrug, or a metabolite thereof.

Another useful compound is

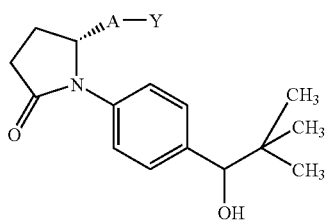

or a pharmaceutically acceptable salt, prodrug, or a metabolite thereof.

Another useful compound is

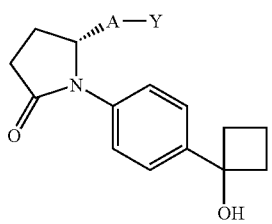

or a pharmaceutically acceptable salt, prodrug, or a metabolite thereof.

Another compound comprises

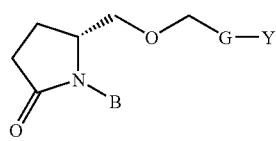

or a pharmaceutically acceptable salt, prodrug, or a metabolite thereof;
wherein G is 1,3-interaryl or interheteroaryl, or —(CH$_2$)$_3$—.

Another compound comprises

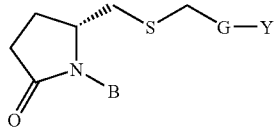

or a pharmaceutically acceptable salt, prodrug, or a metabolite thereof,
wherein G is 1,3-interaryl or interheteroaryl, or —(CH$_2$)$_3$—.

Another compound comprises

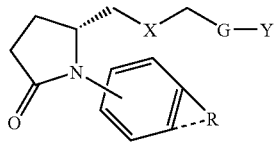

or a pharmaceutically acceptable salt, prodrug, or a metabolite thereof;
wherein a dashed line indicates the presence or absence of a bond;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

In one embodiment A is —S(CH$_2$)$_3$S(CH$_2$)$_2$— and B is phenyl.

In another embodiment A is —(CH$_2$)$_4$OCH$_2$— and B is phenyl.

In another embodiment A is cis —CH$_2$CH=CH—CH$_2$OCH$_2$— and B is phenyl.

In another embodiment A is —CH$_2$CH≡CH—CH$_2$OCH$_2$— and B is phenyl.

In another embodiment A is —(CH$_2$)$_2$S(CH$_2$)$_3$— and B is phenyl.

In another embodiment A is —CH$_2$-Ph-OCH$_2$—, wherein Ph is interphenylene, and B is phenyl.

In another embodiment A is —CH$_2$-mPh-OCH$_2$—, wherein mPh is m-interphenylene, and B is phenyl.

In another embodiment A is —CH$_2$—O—(CH$_2$)$_4$— and B is phenyl.

In another embodiment A is —CH$_2$—O—CH$_2$—Ar—, wherein Ar is 2,5-interthienylene, and B is phenyl.

In another embodiment A is —CH$_2$—O—CH—Ar—, wherein Ar is 2,5-interfurylene, and B is phenyl.

As mentioned before, phenyl in the above embodiments means substituted or unsubstituted phenyl unless indicated otherwise.

In one embodiment A is —S(CH$_2$)$_3$S(CH$_2$)$_2$— and B is (1-hydroxyhexyl)phenyl.

In another embodiment A is —(CH$_2$)$_4$OCH$_2$— and B is (1-hydroxyhexyl)phenyl.

In another embodiment A is cis —CH$_2$CH=CH—CH$_2$OCH$_2$— and B is (1-hydroxyhexyl)phenyl.

In another embodiment A is —CH$_2$CH≡CH—CH$_2$OCH$_2$— and B is (1-hydroxyhexyl)phenyl.

In another embodiment A is —(CH$_2$)$_2$S(CH$_2$)$_3$— and B is (1-hydroxyhexyl)phenyl.

In another embodiment A is —CH$_2$-Ph-OCH$_2$—, wherein Ph is interphenylene, and B is (1-hydroxyhexyl)phenyl.

In another embodiment A is —CH₂-mPh-OCH₂—, wherein mPh is m-interphenylene, and B is (1-hydroxyhexyl)phenyl.

In another embodiment A is —CH₂—O—(CH₂)₄— and B is (1-hydroxyhexyl)phenyl.

In another embodiment A is —CH₂—O—CH₂—Ar—, wherein Ar is 2,5-interthienylene, and B is (1-hydroxyhexyl)phenyl.

In another embodiment A is —CH₂—O—CH₂—Ar—, wherein Ar is 2,5-interfurylene, and B is (1-hydroxyhexyl)phenyl.

In another embodiment A is —S(CH₂)₃S(CH₂)₂— and B is (1-hydroxy-2,2-dimethylpropyl)phenyl.

In another embodiment A is —(CH₂)₄OCH₂— and B is (1-hydroxy-2,2-dimethylpropyl)phenyl.

In another embodiment A is cis —CH₂CH═CH—CH₂OCH₂— and B is (1-hydroxy-2,2-dimethylpropyl)phenyl.

In another embodiment A is —CH₂CH≡CH—CH₂OCH₂— and B is (1-hydroxy-2,2-dimethylpropyl)phenyl.

In another embodiment A is —(CH₂)₂S(CH₂)₃— and B is (1-hydroxy-2,2-dimethylpropyl)phenyl.

In another embodiment A is —CH₂-Ph-OCH₂—, wherein Ph is interphenylene, and B is (1-hydroxy-2,2-dimethylpropyl)phenyl.

In another embodiment A is —CH₂-mPh-OCH₂—, wherein mPh is m-interphenylene, and B is (1-hydroxy-2,2-dimethylpropyl)phenyl.

In another embodiment A is —CH₂—O—(CH₂)₄— and B is (1-hydroxy-2,2-dimethylpropyl)phenyl.

In another embodiment A is —CH₂—O—CH₂—Ar—, wherein Ar is 2,5-interthienylene, and B is (1-hydroxy-2,2-dimethylpropyl)phenyl.

In another embodiment A is —CH₂—O—CH₂—Ar—, wherein Ar is 2,5-interfurylene, and B is (1-hydroxy-2,2-dimethylpropyl)phenyl.

In another embodiment A is —S(CH₂)₃S(CH₂)₂— and B is (1-hydroxy-2-methylpropyl)phenyl.

In another embodiment A is —(CH₂)₄OCH₂— and B is (1-hydroxy-2-methylpropyl)phenyl.

In another embodiment A is cis —CH₂CH═CH—CH₂OCH₂— and B is (1-hydroxy-2-methylpropyl)phenyl.

In another embodiment A is —CH₂C≡CH—CH₂OCH₂— and B is (1-hydroxy-2-methylpropyl)phenyl.

In another embodiment A is —(CH₂)₂S(CH₂)₃— and B is (1-hydroxy-2-methylpropyl)phenyl.

In another embodiment A is —CH₂-Ph-OCH₂—, wherein Ph is interphenylene, and B is (1-hydroxy-2-methylpropyl)phenyl.

In another embodiment A is —CH₂-mPh-OCH₂—, wherein mPh is m-interphenylene, and B is (1-hydroxy-2-methylpropyl)phenyl.

In another embodiment A is —CH₂—O—(CH₂)₄— and B is (1-hydroxy-2-methylpropyl)phenyl.

In another embodiment A is —CH₂—O—CH₂—Ar—, wherein Ar is 2,5-interthienylene, and B is (1-hydroxy-2-methylpropyl)phenyl.

In another embodiment A is —CH₂—O—CH₂—Ar—, wherein Ar is 2,5-interfurylene, and B is (1-hydroxy-2-methylpropyl)phenyl.

In another embodiment A is —S(CH₂)₃S(CH₂)₂— and B is (hydroxymethyl)phenyl.

In another embodiment A is —(CH₂)₄OCH₂— and B is (hydroxymethyl)phenyl.

In another embodiment A is cis —CH₂CH═CH—CH₂OCH₂— and B is (hydroxymethyl)phenyl.

In another embodiment A is —CH₂CH≡CH—CH₂OCH₂— and B is (hydroxymethyl)phenyl.

In another embodiment A is —(CH₂)₂S(CH₂)₃— and B is (hydroxymethyl)phenyl.

In another embodiment A is —CH₂-Ph-OCH₂—, wherein Ph is interphenylene, and B is (hydroxymethyl)phenyl.

In another embodiment A is —CH₂-mPh-OCH₂—, wherein mPh is m-interphenylene, and B is (hydroxymethyl)phenyl.

In another embodiment A is —CH₂—O—(CH₂)₄— and B is (hydroxymethyl)phenyl.

In another embodiment A is —CH₂—O—CH₂—Ar—, wherein Ar is 2,5-interthienylene, and B is (hydroxymethyl)phenyl.

In another embodiment A is —CH₂—O—CH₂—Ar—, wherein Ar is 2,5-interfurylene, and B is (hydroxymethyl)phenyl.

In another embodiment A is —S(CH₂)₃S(CH₂)₂— and B is [(1-propylcyclobutyl)hydroxymethyl]phenyl.

In another embodiment A is —(CH₂)₄OCH₂— and B is [(1-propylcyclobutyl)hydroxymethyl]phenyl.

In another embodiment A is cis —CH₂CH═CH—CH₂OCH₂— and B is [(1-propylcyclobutyl)hydroxymethyl]phenyl.

In another embodiment A is —CH₂CH≡CH—CH₂OCH₂— and B is [(1-propylcyclobutyl)hydroxymethyl]phenyl.

In another embodiment A is —(CH₂)₂S(CH₂)₃— and B is [(1-propylcyclobutyl)hydroxymethyl]phenyl.

In another embodiment A is —CH₂-Ph-OCH₂—, wherein Ph is interphenylene, and B is [(1-propylcyclobutyl)hydroxymethyl]phenyl.

In another embodiment A is —CH₂-mPh-OCH₂—, wherein mPh is m-interphenylene, and B is [(1-propylcyclobutyl)hydroxymethyl]phenyl.

In another embodiment A is —CH₂—O—(CH₂)₄— and B is [(1-propylcyclobutyl)hydroxymethyl]phenyl.

In another embodiment A is —CH₂—O—CH₂—Ar—, wherein Ar is 2,5-interthienylene, and B is [(1-propylcyclobutyl)hydroxymethyl]phenyl.

In another embodiment A is —CH₂—O—CH₂—Ar—, wherein Ar is 2,5-interfurylene, and B is [(1-propylcyclobutyl)hydroxymethyl]phenyl.

In another embodiment A is —S(CH₂)₃S(CH₂)₂— and B is t-butylphenyl.

In another embodiment A is —(CH₂)₄OCH₂— and B is t-butylphenyl.

In another embodiment A is cis —CH₂CH═CH—CH₂OCH₂— and B is t-butylphenyl.

In another embodiment A is —CH₂CH≡CH—CH₂OCH₂— and B is t-butylphenyl.

In another embodiment A is —(CH₂)₂S(CH₂)₃— and B is t-butylphenyl.

In another embodiment A is —CH₂-Ph-OCH₂—, wherein Ph is interphenylene, and B is t-butylphenyl.

In another embodiment A is —CH₂-mPh-OCH₂—, wherein mPh is m-interphenylene, and B is t-butylphenyl.

In another embodiment A is —CH₂—O—(CH₂)₄— and B is t-butylphenyl.

In another embodiment A is —CH₂—O—CH₂—Ar—, wherein Ar is 2,5-interthienylene, and B is t-butylphenyl.

In another embodiment A is —CH₂—O—CH₂—Ar—, wherein Ar is 2,5-interfurylene, and B is t-butylphenyl.

In another embodiment A is —S(CH₂)₃S(CH₂)₂— and B is (cyclohexylhydroxymethyl)phenyl.

In another embodiment A is —(CH₂)₄OCH₂— and B is (cyclohexylhydroxymethyl)phenyl.

In another embodiment A is cis —CH$_2$CH=CH—CH$_2$OCH$_2$— and B is (cyclohexylhydroxymethyl)phenyl.

In another embodiment A is —CH$_2$CH≡CH—CH$_2$OCH$_2$— and B is (cyclohexylhydroxymethyl)phenyl.

In another embodiment A is —(CH$_2$)$_2$S(CH$_2$)$_3$— and B is (cyclohexylhydroxymethyl)phenyl.

In another embodiment A is —CH$_2$-Ph-OCH$_2$—, wherein Ph is interphenylene, and B is (cyclohexylhydroxymethyl)phenyl.

In another embodiment A is —CH$_2$-mPh-OCH$_2$—, wherein mPh is m-interphenylene, and B is (cyclohexylhydroxymethyl)phenyl.

In another embodiment A is —CH$_2$—O—(CH$_2$)$_4$— and B is (cyclohexylhydroxymethyl)phenyl.

In another embodiment A is —CH$_2$—O—CH$_2$—Ar—, wherein Ar is 2,5-interthienylene, and B is (cyclohexylhydroxymethyl)phenyl.

In another embodiment A is —CH$_2$—O—CH$_2$—Ar—, wherein Ar is 2,5-interfurylene, and B is (cyclohexylhydroxymethyl)phenyl.

In another embodiment A is —S(CH$_2$)$_3$S(CH$_2$)$_2$— and B is (cyclohexylmethyl)phenyl.

In another embodiment A is —(CH$_2$)$_4$OCH$_2$— and B is (cyclohexylmethyl)phenyl.

In another embodiment A is cis —CH$_2$CH=CH—CH$_2$OCH$_2$— and B is (cyclohexylmethyl)phenyl.

In another embodiment A is —CH$_2$CH≡CH—CH$_2$OCH$_2$— and B is (cyclohexylmethyl)phenyl.

In another embodiment A is —(CH$_2$)$_2$S(CH$_2$)$_3$— and B is (cyclohexylmethyl)phenyl.

In another embodiment A is —CH$_2$-Ph-OCH$_2$—, wherein Ph is interphenylene, and B is (cyclohexylmethyl)phenyl.

In another embodiment A is —CH$_2$-mPh-OCH$_2$—, wherein mPh is m-interphenylene, and B is (cyclohexylmethyl)phenyl.

In another embodiment A is —CH$_2$—O—(CH$_2$)$_4$— and B is (cyclohexylmethyl)phenyl.

In another embodiment A is —CH$_2$—O—CH$_2$—Ar—, wherein Ar is 2,5-interthienylene, and B is (cyclohexylmethyl)phenyl.

In another embodiment A is —CH$_2$—O—CH$_2$—Ar—, wherein Ar is 2,5-interfurylene, and B is (cyclohexylmethyl)phenyl.

In another embodiment A is —S(CH$_2$)$_3$S(CH$_2$)$_2$— and B is indanyl.

In another embodiment A is —(CH$_2$)$_4$OCH$_2$— and B is indanyl.

In another embodiment A is cis —CH$_2$CH=CH—CH$_2$OCH$_2$— and B is indanyl.

In another embodiment A is —CH$_2$CH≡CH—CH$_2$OCH$_2$— and B is indanyl.

In another embodiment A is —(CH$_2$)$_2$S(CH$_2$)$_3$— and B is indanyl.

In another embodiment A is —CH$_2$-Ph-OCH$_2$—, wherein Ph is interphenylene, and B is indanyl.

In another embodiment A is —CH$_2$-mPh-OCH$_2$—, wherein mPh is m-interphenylene, and B is indanyl.

In another embodiment A is —CH$_2$—O—(CH$_2$)$_4$— and B is indanyl.

In another embodiment A is —CH$_2$—O—CH$_2$—Ar—, wherein Ar is 2,5-interthienylene, and B is indanyl.

In another embodiment A is —CH$_2$—O—CH$_2$—Ar—, wherein Ar is 2,5-interfurylene, and B is indanyl.

In another embodiment A is —S(CH$_2$)$_3$S(CH$_2$)$_2$— and B is indanolyl.

In another embodiment A is —(CH$_2$)$_4$OCH$_2$— and B is indanolyl.

In another embodiment A is cis —CH$_2$CH=CH—CH$_2$OCH$_2$— and B is indanolyl.

In another embodiment A is —CH$_2$CH≡CH—CH$_2$OCH$_2$— and B is indanolyl.

In another embodiment A is —(CH$_2$)$_2$S(CH$_2$)$_3$— and B is indanolyl.

In another embodiment A is —CH$_2$-Ph-OCH$_2$—, wherein Ph is interphenylene, and B is indanolyl.

In another embodiment A is —CH$_2$-mPh-OCH$_2$—, wherein mPh is m-interphenylene, and B is indanolyl.

In another embodiment A is —CH$_2$—O—(CH$_2$)$_4$— and B is indanolyl.

In another embodiment A is —CH$_2$—O—CH$_2$—Ar—, wherein Ar is 2,5-interthienylene, and B is indanolyl.

In another embodiment A is —CH$_2$—O—CH$_2$—Ar—, wherein Ar is 2,5-interfurylene, and B is indanolyl.

In another embodiment A is —S(CH$_2$)$_3$S(CH$_2$)$_2$— and B is indanonyl.

In another embodiment A is —(CH$_2$)$_4$OCH$_2$— and B is indanonyl.

In another embodiment A is cis —CH$_2$CH=CH—CH$_2$OCH$_2$— and B is indanonyl.

In another embodiment A is —CH$_2$CH≡CH—CH$_2$OCH$_2$— and B is indanonyl.

In another embodiment A is —(CH$_2$)$_2$S(CH$_2$)$_3$— and B is indanonyl.

In another embodiment A is —CH$_2$-Ph-OCH$_2$—, wherein Ph is interphenylene, and B is indanonyl.

In another embodiment A is —CH$_2$-mPh-OCH$_2$—, wherein mPh is m-interphenylene, and B is indanonyl.

In another embodiment A is —CH$_2$—O—(CH$_2$)$_4$— and B is indanonyl.

In another embodiment A is —CH$_2$—O—CH$_2$—Ar—, wherein Ar is 2,5-interthienylene, and B is indanonyl.

In another embodiment A is —CH$_2$—O—CH$_2$—Ar—, wherein Ar is 2,5-interfurylene, and B is indanonyl.

In another embodiment A is —S(CH$_2$)$_3$S(CH$_2$)$_2$— and B is (1-hydroxycyclobutyl)phenyl.

In another embodiment A is —(CH$_2$)$_4$OCH$_2$— and B is (1-hydroxycyclobutyl)phenyl.

In another embodiment A is cis —CH$_2$CH=CH—CH$_2$OCH$_2$— and B is (1-hydroxycyclobutyl)phenyl.

In another embodiment A is —CH$_2$CH≡CH—CH$_2$OCH$_2$— and B is (1-hydroxycyclobutyl)phenyl.

In another embodiment A is —(CH$_2$)$_2$S(CH$_2$)$_3$— and B is (1-hydroxycyclobutyl)phenyl.

In another embodiment A is —CH$_2$-Ph-OCH$_2$—, wherein Ph is interphenylene, and B is (1-hydroxycyclobutyl)phenyl.

In another embodiment A is —CH$_2$-mPh-OCH$_2$—, wherein mPh is m-interphenylene, and B is (1-hydroxycyclobutyl)phenyl.

In another embodiment A is —CH$_2$—O—(CH$_2$)$_4$— and B is (1-hydroxycyclobutyl)phenyl.

In another embodiment A is —CH$_2$—O—CH$_2$—Ar—, wherein Ar is 2,5-interthienylene, and B is (1-hydroxycyclobutyl)phenyl.

In another embodiment A is —CH$_2$—O—CH$_2$—Ar—, wherein Ar is 2,5-interfurylene, and B is (1-hydroxycyclobutyl)phenyl.

In another embodiment A is —S(CH$_2$)$_3$S(CH$_2$)$_2$— and B is (2-methyl-3-hydroxypropyl)phenyl.

In another embodiment A is —(CH$_2$)$_4$OCH$_2$— and B is (2-methyl-3-hydroxypropyl)phenyl.

In another embodiment A is cis —CH$_2$CH=CH—CH$_2$OCH$_2$— and B is (2-methyl-3-hydroxypropyl)phenyl.

In another embodiment A is —CH$_2$CH≡CH—CH$_2$OCH$_2$— and B is (2-methyl-3-hydroxypropyl)phenyl.

In another embodiment A is —(CH$_2$)$_2$S(CH$_2$)$_3$— and B is (2-methyl-3-hydroxypropyl)phenyl.

In another embodiment A is —CH$_2$-Ph-OCH$_2$—, wherein Ph is interphenylene, and B is (2-methyl-3-hydroxypropyl)phenyl.

In another embodiment A is —CH$_2$-mPh-OCH$_2$—, wherein mPh is m-interphenylene, and B is (2-methyl-3-hydroxypropyl)phenyl.

In another embodiment A is —CH$_2$—O—(CH$_2$)$_4$— and B is (2-methyl-3-hydroxypropyl)phenyl.

In another embodiment A is —CH$_2$—O—CH$_2$—Ar—, wherein Ar is 2,5-interthienylene, and B is (2-methyl-3-hydroxypropyl)phenyl.

In another embodiment A is —CH$_2$—O—CH$_2$—Ar—, wherein Ar is 2,5-interfurylene, and B is (2-methyl-3-hydroxypropyl)phenyl.

In another embodiment A is —S(CH$_2$)$_3$S(CH$_2$)$_2$— and B is (1-hydroxy-2-phenylethyl)phenyl.

In another embodiment A is —(CH$_2$)$_4$OCH$_2$— and B is (1-hydroxy-2-phenylethyl)phenyl.

In another embodiment A is cis —CH$_2$CH═CH—CH$_2$OCH$_2$— and B is (1-hydroxy-2-phenylethyl)phenyl.

In another embodiment A is —CH$_2$CH═CH—CH$_2$OCH$_2$— and B is (1-hydroxy-2-phenylethyl)phenyl.

In another embodiment A is —(CH$_2$)$_2$S(CH$_2$)$_3$— and B is (1-hydroxy-2-phenylethyl)phenyl.

In another embodiment A is —CH$_2$-Ph-OCH$_2$—, wherein Ph is interphenylene, and B is (1-hydroxy-2-phenylethyl)phenyl.

In another embodiment A is —CH$_2$-mPh-OCH$_2$—, wherein mPh is m-interphenylene, and B is (1-hydroxy-2-phenylethyl)phenyl.

In another embodiment A is —CH$_2$—O—(CH$_2$)$_4$— and B is (1-hydroxy-2-phenylethyl)phenyl.

In another embodiment A is —CH$_2$—O—CH$_2$—Ar—, wherein Ar is 2,5-interthienylene, and B is (1-hydroxy-2-phenylethyl)phenyl.

In another embodiment A is —CH$_2$—O—CH$_2$—Ar—, wherein Ar is 2,5-interfurylene, and B is (1-hydroxy-2-phenylethyl)phenyl.

The compounds of disclosed herein are useful for the prevention or treatment of glaucoma or ocular hypertension in mammals, or for the manufacture of a medicament for the treatment of glaucoma or ocular hypertension. A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

These compounds are also useful for growing hair, including one or more of: increasing the number of individual hairs, increasing the length of individual hairs, and increasing the width or thickness of individual hairs. These compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

For the purposes of this disclosure, "treat," "treating," or "treatment" refer to the use of a compound, composition, therapeutically active agent, or drug in the diagnosis, cure, mitigation, treatment, prevention of disease or other undesirable condition.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

Synthetic Methods

The esterification method exemplified below is useful for a range of carboxylic acids. For example, any carboxylic acid prepared as described in U.S. patent application Ser. No. 10/599,046, filed on Sep. 18, 2006, incorporated by reference herein, may be used.

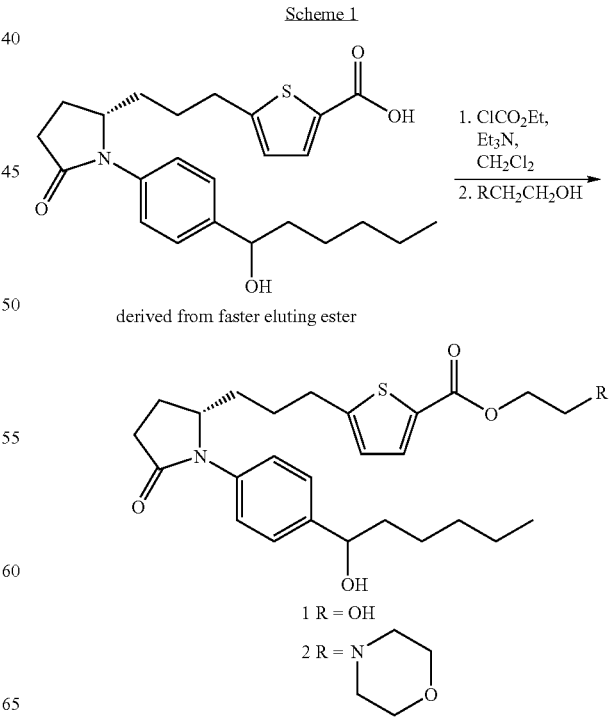

Scheme 1

5-(3-{(S)-1-[4-(1-Hydroxyhexyl)-phenyl]-5-oxo-pyrrolidin-2-yl}-propyl)-thiophene-2-carboxylic acid 2-hydroxyethyl ester (1)

Triethylamine (17.5 µL, 0.13 mmol) and ethyl chloroformate (6 µL, 0.063 mmol) were added sequentially to a solution 5-(3-{(S)-1-[4-(1-hydroxyhexyl)-phenyl]-5-oxo-pyrrolidin-2-yl}-propyl)-thiophene-2-carboxylic acid (derived from the faster eluting [HPLC] ester diastereomer, see U.S. Ser. No. 10/599,046 or U.S. Provisional Patent Application No. 60/777,506, filed on Feb. 28, 2006, incorporated by reference herein, 18 mg, 0.042 mmol) in $CH_2Cl_2$ (0.6 mL) at 0° C. The mixture was allowed to warm to room temperature. After 30 min at room temperature, ethylene glycol (25 µL, 0.45 mmol) was added. After stirring overnight at room temperature, the reaction mixture was concentrated under a stream of nitrogen. The residue was diluted with EtOAc (20 mL) and washed with $H_2O$ (2×5 mL) and brine (5 mL). The organic phase was dried ($Na_2SO_4$), filtered and concentrated in vacuo. Purification of the residue by flash column chromatography on silica gel ($CH_2Cl_2 \rightarrow 10\%$ MeOH/$CH_2Cl_2$, gradient) afforded 8.5 mg (43%) of the title compound (1).

5-(3-{(S)-1-[4-(1-Hydroxyhexyl)-phenyl]-5-oxo-pyrrolidin-2-yl}-propyl)-thiophene-2-carboxylic acid 2-morpholin-4-yl-ethyl ester (2)

Triethylamine (17.5 µL, 0.13 mmol) and ethyl chloroformate (6 µL, 0.063 mmol) were added sequentially to a solution of 5-(3-{(S)-1-[4-(1-hydroxyhexyl)-phenyl]-5-oxo-pyrrolidin-2-yl}-propyl)-thiophene-2-carboxylic acid (derived from the faster eluting [HPLC] ester diastereomer, see U.S. Ser. No. 10/599,046 or U.S. 60/777,506, 18 mg, 0.042 mmol) in $CH_2Cl_2$ (0.6 mL) at 0° C. The mixture was allowed to warm to room temperature. After 30 min at room temperature, 4-(2-hydroxyethyl)morpholine (51 µL, 0.42 mmol) was added. After stirring overnight at room temperature, the reaction mixture was concentrated under a stream of nitrogen. The residue was diluted with EtOAc (20 mL) and washed with $H_2O$ (2×5 mL) and brine (5 mL). The organic phase was dried ($Na_2SO_4$), filtered and concentrated in vacuo. Purification of the residue by flash column chromatography on silica gel ($CH_2Cl_2 \rightarrow 10\%$ MeOH/$CH_2Cl_2$, gradient) afforded 8.5 mg (37%) of the title compound (2).

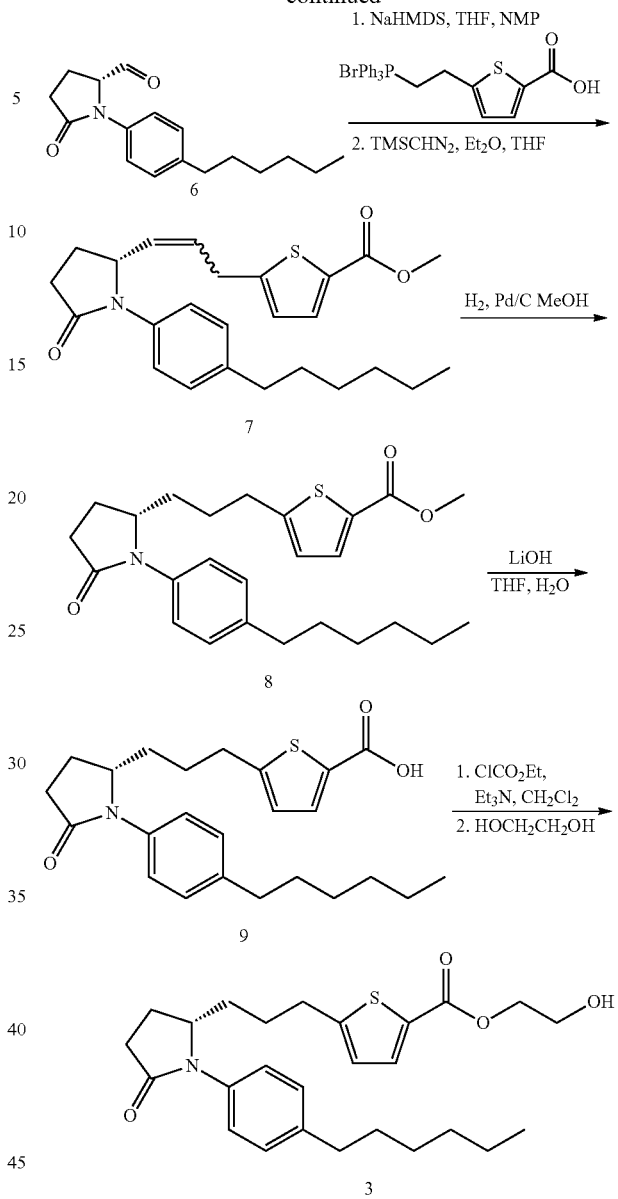

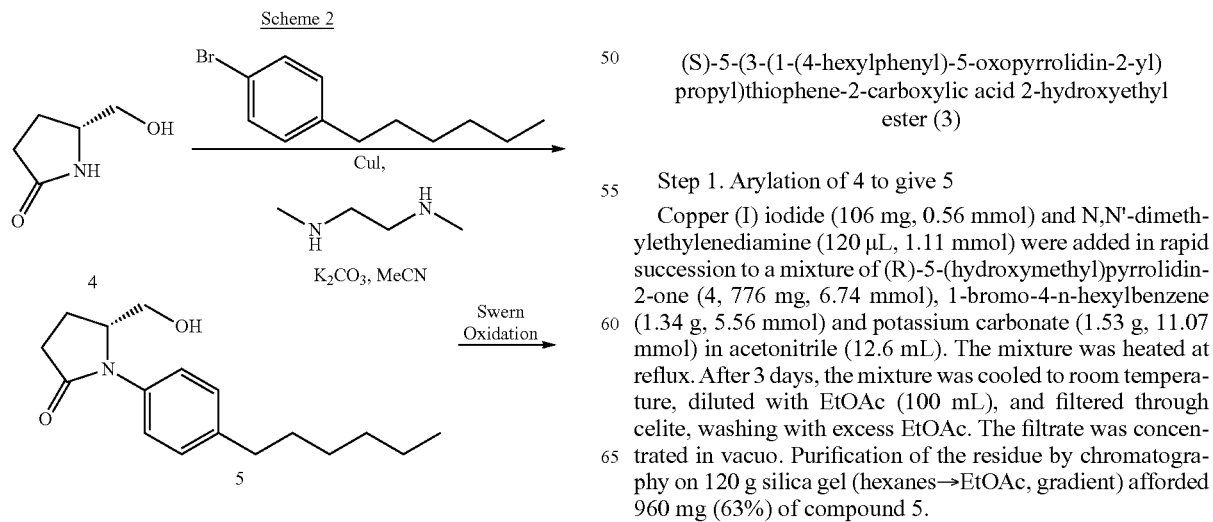

(S)-5-(3-(1-(4-hexylphenyl)-5-oxopyrrolidin-2-yl)propyl)thiophene-2-carboxylic acid 2-hydroxyethyl ester (3)

Step 1. Arylation of 4 to give 5

Copper (I) iodide (106 mg, 0.56 mmol) and N,N'-dimethylethylenediamine (120 µL, 1.11 mmol) were added in rapid succession to a mixture of (R)-5-(hydroxymethyl)pyrrolidin-2-one (4, 776 mg, 6.74 mmol), 1-bromo-4-n-hexylbenzene (1.34 g, 5.56 mmol) and potassium carbonate (1.53 g, 11.07 mmol) in acetonitrile (12.6 mL). The mixture was heated at reflux. After 3 days, the mixture was cooled to room temperature, diluted with EtOAc (100 mL), and filtered through celite, washing with excess EtOAc. The filtrate was concentrated in vacuo. Purification of the residue by chromatography on 120 g silica gel (hexanes→EtOAc, gradient) afforded 960 mg (63%) of compound 5.

Step 2. Oxidation of 5 to give 6

DMSO (315 μL, 4.44 mmol) was added to a −78° C. solution of oxalyl chloride (1.1 mL of a 2.0 M solution in $CH_2Cl_2$, 2.2 mmol) and $CH_2Cl_2$ (15 mL). After 15 min at −78° C., a solution of 5 (489 mg, 1.78 mmol) in $CH_2Cl_2$ (15 mL) was added via cannula. After 15 min at −78° C., triethylamine (1.98 mL, 14.2 mmol) was added dropwise and the mixture was allowed to warm to 0° C. After 45 min at 0° C., the reaction was diluted with $CH_2Cl_2$ (50 mL) and saturated aqueous $NaHCO_3$ (100 mL) was added. The phases were separated and the aqueous phase was extracted with $CH_2Cl_2$ (2×100 mL). The combined organic phase was dried ($Na_2SO_4$), filtered and concentrated in vacuo. The crude residue, compound 6, was used in the next step without further purification.

Step 3. Wittig reaction of 6 and alkylation to give 7

Sodium bis(trimethylsilyl)amide (3.60 mL of a 1.0 M solution in THF, 3.60 mmol) was added to a solution of [2-(5-carboxy-thiophen-2-yl)-ethyl]-priphenylphosphonium bromide (see U.S. Provisional Patent Application No. 60/894,267, filed Mar. 12, 2007, incorporated by reference herein, 895 mg, 1.80 mmol) in 1-methyl-2-pyrrolidinone (NMP, 3.6 mL) at 0° C. The resulting deep red solution was stirred at 0° C. for 30 min then was cooled to −20° C. A solution of 6 (−1.78 mmol crude) in THF (3.6 mL) was added to the red ylide solution by cannula. After 30 min at −20° C., the mixture was allowed to warm to 0° C. After 30 min at 0° C. the reaction was quenched by the addition of saturated aqueous $NH_4Cl$ (50 mL) and extracted with EtOAc (3×100 mL). The combined organic phase was dried ($Na_2SO_4$), filtered and concentrated in vacuo. The crude residue dissolved in THF (18 mL) and cooled to 0° C. (Trimethylsilyl)diazomethane (4.4 mL of a 2.0 M solution in $Et_2O$, 8.8 mmol) was added and the mixture was allowed to warm to room temperature. After 30 min at room temperature the mixture was concentrated in vacuo. Purification of the residue by chromatography on 80 g silica gel (hexanes→EtOAc, gradient) afforded 256 mg (34% from 5) of compound 7.

Step 4. Hydrogenation of 7 to give 8

Palladium on carbon (10 wt. %, 53 mg) was added to a solution of 7 (213 mg, 0.50 mmol) in MeOH (5.0 mL). A hydrogen atmosphere was established by evacuating and refilling with hydrogen (5×) and the mixture was stirred under a balloon of hydrogen. After 42 h, the reaction mixture was filtered through celite, washing with excess MeOH. The filtrate was concentrated in vacuo to afford 182 mg (85%) of 8.

Step 5. Saponification of 8 to give 9

Lithium hydroxide (2.1 mL of a 1.0 M solution in water, 2.1 mmol) was added to a solution of 8 (182 mg, 0.42 mmol) in THF (4.2 mL) and the mixture was heated at 40° C. After 18 h at 40° C., the mixture was cooled concentrated in vacuo. The residue was diluted with water (5 mL) and acidified with 1 N aqueous HCl (3 mL). The mixture was extracted with EtOAc (3×30 mL). The combined extracts were washed with brine (20 mL), dried ($Na_2SO_4$), filtered and concentrated in vacuo.

Purification of the crude residue by chromatography on 12 g silica gel ($CH_2Cl_2$→15% $MeOH/CH_2Cl_2$, gradient) afforded 140 mg (80%) of 9.

Step 6. Esterification of 9 to give 3

Triethylamine (60 μL, 0.43 mmol) and ethyl chloroformate (21 μL, 0.22 mmol) were added sequentially to a solution of 9 (60 mg, 0.145 mmol) in $CH_2Cl_2$ (2 mL) at 0° C. The mixture was allowed to warm to rt. After 30 min at rt, ethylene glycol (81 μL, 1.45 mmol) was added. After stirring 3 days at room temperature, the reaction mixture was concentrated under a stream of nitrogen. The residue was diluted with EtOAc (50 mL) and washed with $H_2O$ (2×25 mL) and brine (25 mL). The organic phase was dried ($Na_2SO_4$), filtered and concentrated in vacuo. Purification of the residue by chromatography on 4 g silica gel (hexanes→EtOAc, gradient) afforded 28 mg (42%) of the title compound (3).

In Vivo Experimental Data

U.S. Pat. No. 7,091,231 describes the methods used for these in vivo tests.

5-(3-{(S)-1-[4-(1-Hydroxyhexyl)-phenyl]-5-oxo-pyrrolidin-2-yl}-propyl)-thiophene-2-carboxylic acid 2-hydroxyethyl ester (1) was tested in normotensive dogs at 0.003%, dosing once daily for 5 days. The maximum intraocular pressure (IOP) decrease from baseline was 4.4 mmHg (32%) at 30 h; the maximum ocular surface hyperemia (OSH) score was 0.9 at 30 h. This compound was also tested in laser-induced hypertensive monkeys, using one single day dose. At 0.003%, the maximum IOP decrease from baseline was 13.4 mmHg (38%) at 24 h. Compound 1 was also tested in normotensive dogs at 0.001%, dosing once daily for 5 days. The maximum intraocular pressure (IOP) decrease from baseline was 3.75 mmHg (23%) at 76 h; the maximum ocular surface hyperemia (OSH) score was 1.1 at 74 h. Compound 1 was also tested in laser-induced hypertensive monkeys, using one single day dose. At 0.001%, the maximum IOP decrease from baseline was 12.7 mmHg (31%) at 24 h.

5-(3-{(S)-1-[4-(1-Hydroxyhexyl)-phenyl]-5-oxo-pyrrolidin-2-yl}-propyl)-thiophene-2-carboxylic acid 2-morpholin-4-yl-ethyl ester (2) was tested in normotensive dogs at 0.003%, dosing once daily for 5 days. The maximum intraocular pressure (IOP) decrease from baseline was 5.9 mmHg (36%) at 52 h; the maximum ocular surface hyperemia (OSH) score was 1.1 at 50 h. This compound was also tested in laser-induced hypertensive monkeys, using one single day dose. At 0.003%, the maximum IOP decrease from baseline was 20 mmHg (53%) at 24 h.

What is claimed is:

1. A compound of the formula

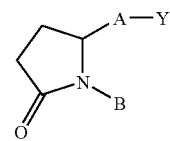

or a pharmaceutically acceptable salt thereof;
wherein
Y is —$CO_2(CH_2)_2OH$ or

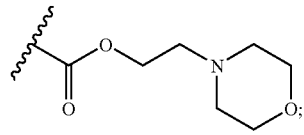

A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein 1-$CH_2$— may be replaced by S or O, and 1-$CH_2$—$CH_2$ may be replaced by —CH=CH— or C≡C; and B is aryl or heteroaryl.

2. The compound of claim 1 of the formula

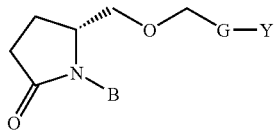

or a pharmaceutically acceptable salt thereof;
wherein G is 1,3-interaryl or interheteroaryl, or —(CH$_2$)$_3$—.

3. The compound of claim 1 wherein B is phenyl.
4. The compound of claim 1 wherein B is alkylphenyl.
5. The compound of claim 4 wherein B is p-t-butylphenyl.
6. The compound of claim 3 wherein B is hydroxyalkylphenyl.
7. The compound of claim 1 of the formula

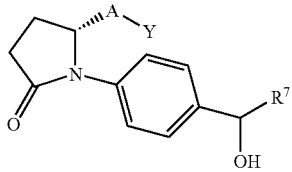

or a pharmaceutically acceptable salt thereof,
wherein R$^7$ is linear alkyl comprising 3, 4, 5, 6 or 7 carbon atoms.

8. The compound of claim 1 of the formula

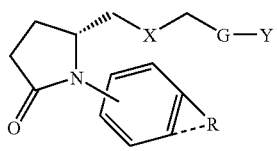

or a pharmaceutically acceptable salt thereof;
wherein a dashed line indicates the presence or absence of a bond;
R is hydrocarbyl or hydroxyhydrocarbyl having from 1 to 12 carbon atoms;
X is CH$_2$, O, or S; and
G is 1,3-interaryl or interheteroaryl, or —(CH$_2$)$_3$—.

9. The compound of claim 8 of the formula

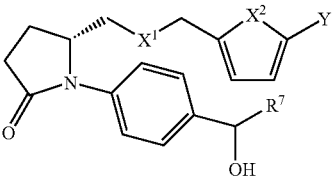

or a pharmaceutically acceptable salt thereof,
wherein X$^1$ and X$^2$ are independently CH, O, or S; and
R$^7$ is linear alkyl comprising from 3 to 7 carbon atoms.

10. The compound of claim 1, said compound comprising

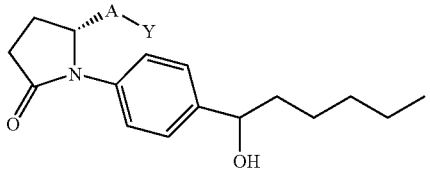

or a pharmaceutically acceptable salt thereof.

11. The compound of claim 10 of the formula

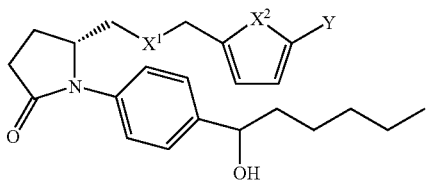

or a pharmaceutically acceptable salt thereof,
wherein X$^1$ and X$^2$ are independently CH, O, or S.

12. The compound according to claim 1 wherein Y is —CO$_2$(CH$_2$)$_2$OH.

13. The compound according to claim 1 wherein Y is

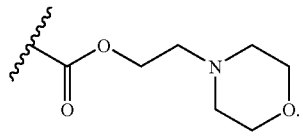

14. A composition comprising a compound according to claim 1, wherein said composition is a liquid which is ophthalmically acceptable.

15. A method of treating glaucoma or ocular hypertension comprising administering a compound according to claim 1 to a mammal in need thereof.

16. A method of growing hair or improving the appearance of hair comprising administering a compound according to claim 1 to a mammal in need thereof.

* * * * *